US006288783B1

(12) United States Patent
Auad

(10) Patent No.: US 6,288,783 B1
(45) Date of Patent: Sep. 11, 2001

(54) FLUID ANALYSIS SYSTEM AND METHOD, FOR ANALYZING CHARACTERISTIC PROPERTIES OF A FLUID

(75) Inventor: Rogerio Batista Auad, Porto Alegre (BR)

(73) Assignee: Renner Herrmann S.A., Porto Alegre-RS (BR)

( * ) Notice: Subject to any disclaimer, the term of this patent is extended or adjusted under 35 U.S.C. 154(b) by 0 days.

(21) Appl. No.: 09/284,290

(22) PCT Filed: Oct. 15, 1996

(86) PCT No.: PCT/BR96/00046

§ 371 Date: Sep. 27, 1999

§ 102(e) Date: Sep. 27, 1999

(87) PCT Pub. No.: WO98/16822

PCT Pub. Date: Apr. 23, 1998

(51) Int. Cl.$^7$ ................................................ G01N 21/85
(52) U.S. Cl. .................... 356/410; 356/436; 356/440; 356/246
(58) Field of Search ................................. 356/436, 440, 356/246, 410

(56) References Cited

U.S. PATENT DOCUMENTS

| 3,740,156 | 6/1973 | Heigl et al. ........................ 356/204 |
| 4,165,179 | * 8/1979 | Sato .................................. 356/246 |
| 4,451,152 | * 5/1984 | Topol et al. ........................ 356/440 |
| 4,818,103 | * 4/1989 | Thomas et al. ...................... 356/72 |
| 5,069,552 | * 12/1991 | Cramer et al. ...................... 356/440 |
| 5,673,114 | * 9/1997 | Ushio ................................ 356/432 |

FOREIGN PATENT DOCUMENTS

| 2 414 162 | 10/1974 | (DE) . |
| 25 25 701 A1 | 12/1976 | (DE) . |
| 4015066 A1 | 11/1991 | (DE) . |
| 302 009 A1 | 2/1989 | (EP) . |
| 304 172 A2 | 2/1989 | (EP) . |

* cited by examiner

*Primary Examiner*—Frank G. Font
*Assistant Examiner*—Roy M Punnoose
(74) *Attorney, Agent, or Firm*—Smith, Gambrell & Russell, LLP

(57) ABSTRACT

A fluid analysis system, for analyzing a specified physical characteristic of a fluid, and a method for the same, the system having a sampling region in communication with a fluid inlet to permit feeding of the fluid between opposed fluid contact surface to form a fluid film with a thickness defined by the distance between the opposed surfaces. A film irradiator irradiates the film with electromagnetic radiation in order to produce an interaction radiation containing information associated with the specified physical characteristic of the fluid, a receptor for receiving the interaction radiation, and a detector associated with the receptor for detecting the interaction radiation. At least one of the opposed fluid surfaces is pervious to electromagnetic radiation.

13 Claims, 8 Drawing Sheets

FLUID ANALYSIS SYSTEM AND METHOD, FOR ANALYZING CHARACTERISTIC PROPERTIES OF A FLUID

TECHNICAL FIELD

The present invention relates to a system and method for rapidly analysing the characteristic properties of fluids such as paints, enamels and dyes, amongst others, so that adjustments can be made to the fluid in order to achieve a desired target physical property thereof, such as its colour, opacity, hue, saturation, luminosity, density, viscosity and/or temperature.

BACKGROUND ART

Properties such as those listed above are used to evaluate the quality or performance of a fluid such as paint. For example, the visual aspect given to a painted surface for a determined illumination depends on the colour of the paint used to paint the surface. Another important property is the opacity, or hiding power, of the paint which indicates the capacity of the paint, for a determined paint film thickness in the dry state, to hide the background colour of the surface on which it is painted.

Both colour and opacity are the objects of product control in paint factories, where visual or spectrophotometric techniques are presently used to analyse the paint. The techniques of the state of the art utilise a basically manual process, where paints are mixed, then sprayed onto a substrate and allowed to dry or are cured after which they are subjected to analysis. This process is extremely time consuming, the standard time taken to analyse a paint being of the order of 36 hours.

Paint manufacturing processes normally use pigment pastes which, when mixed in sufficient proportions, result in the final desired colour. The opacity of the paint is adjusted usually by the addition of resin (transparent varnish) to the mixture, in proportion to the degree of opacity desired.

There are, at present, two methods available for supplying paint to the market: the traditional so-called "factory pack" method, where a paint is produced and has its physical properties (colour, opacity and viscosity) adjusted in the factory, using the techniques mentioned above; and the commercial "mixing" method, where the paint is produced, at the point of sale, by mixing a number of coloured bases—paints having a specified colour such as is used in the CMYK (cyan, magenta, yellow and black) system—in specified proportions to produce the desired colour. This second method brings advantages to both the supplier and the client, making it possible for a large quantity of standard colours and shades to be offered from a reduced stock of coloured bases.

Obviously, these bases must be rigorously controlled with regard to their colour and shade, so that, for a specified proportion of paints mixed together, the resulting paint colour and shade does not vary significantly from one batch of paint to another.

It should also be possible to obtain "factory pack" paints using the "mixing" method, but this relies on the coloured bases having their colorific properties strictly controlled.

In the "mixing" method, the coloured bases (mixtures of pigments, resins, solvents and other additives) have their hues and saturations adjusted by so-called "cutting" of the base by mixing it with a determined proportion of a standard base—a white, black or green base. Once the coloured base has been mixed, it is applied to a surface and allowed to dry or is cured, after which the colorific properties are measured. Comparison of these measured properties with those of a standard base, provide the parameters for whatever adjustment is needed.

This method of comparing the coloured base with a standard base is necessary due to the inherent variability of the batches of pigments supplied to paint manufacturers, as well as to variations in the base fabrication process. For example, one coloured base may have a tinting strength greater than the same coloured base from a different batch. In this case, if both bases are cut with the same proportion of a standard white base, the coloured base having the higher tinting strength will develop a more intense colour.

The technique of mixing or cutting a coloured base with a standard white base, so called desaturation, is necessary because, in their natural state, the concentration of the pigments is such that there is not a sufficient distinction between them in terms of tinting strength and hue, they are chromatically saturated. Therefore, cutting of these chromatically saturated pigments with a standard white base has a "zoom" effect, allowing the various properties of the paint to be measured effectively.

One of the problems with the cutting technique is that a standard white base has to be maintained, and, as with the coloured bases, this base comprises pigments dispersed in resins, solvents and other additives, which in general are not stable. These dispersions of pigments are susceptible to the problems of reaglomoration, sedimentation, evaporation of the solvent—with a consequent increase in concentration—contamination, not to mention problems of variability with atmospheric conditions. Therefore, as with the coloured bases, a pheric conditions. Therefore, as with the coloured bases, a problem arises with respect to the calibration of the properties of the standard base.

In the present state of the art, the standard white base is standardised with respect to either a standard black or a standard green base, which in turn has been standardised with respect to a prior standard white base, and so on, ad infinitum.

A further problem that arises with respect to the present state of the art in the measurement of paint properties is that, as mentioned above, the colorific properties of the paint are measured after it has been applied to a surface and either cured or dried. Thus, the perceived properties of the paint rely on the thickness of the layer applied to the surface, and to the properties of the surface itself, which means that, in order to avoid misinterpretation of the results, due to the influence of the colour and hue of the surface, it is essential that the thickness of the paint applied to the surface be rigorously controlled.

Other sources of error that may be introduced into the measurement of paint properties are: in the weighing of the components of the paint; the pressure of the spray used to apply the paint to the surface; the drying temperature; the method of preparation of the surface; the relative humidity of the air; etc..

There are a number of prior art documents which describe devices and processes for measuring the physical properties of paints and other fluids, however, non of these devices or processes allow the true automation of the paint or fluid production process, requiring manual intervention in order to produce either a reflection spectrum or a transmission spectrum, but not both, of the fluid under analysis. There follows a brief description of some such prior art documents:

DE 25 25 701 describes an apparatus for measuring the colour of paint in its liquid form, by forming a film of paint that is irradiated and the reflected radiation is analysed spectrophotometrically. The film is formed by allowing a stream of paint to impinge on a disc which is spinning about a horizontal axis. The paint forms a film as it runs down the disc under the force of gravity due to the centrifugal force provided by the spinning disc. It is not possible to adjust automatically the thickness of the film of paint in order to provide consistent optimised measurements of the paint properties, and the apparatus is only suitable for making measurements of the reflection spectrum of the paint.

EP 0 304 172 describes a method and apparatus for measuring the colour properties of a paint by irradiating a sample volume of the paint, which is subjected to shearing forces and turbulence, and analysing the radiation reflected from the sample. According to this document, the application of shearing forces to the volume of paint under analysis is advantageous in that deflocculation of the pigments within the paint does not occur. However, the apparatus described in this document is unsuitable for the measurement of the transmission spectrum of a paint, since a film of paint is not formed, and is unsuited to use on-line in a paint production process.

JP 02059627 describes a method and device for colorimetric analysis of a paint by forming a liquid film and measuring its "spectral reflectance". The film is formed by inserting a bar into a paint reservoir and lifting it out to pull a film of paint out of the reservoir by means of surface tension. The apparatus is unsuitable for use on-line in a paint production process, and can be used only for making measurements of the reflection spectrum, it being impossible to control the thickness of the film.

EP 0 302 009 describes a fluid sampling cell for use in measuring the transmission spectrum of a high temperature fluid. The sampling cell comprises a sampling region through which a fluid is allowed to flow, and the sampling region has a film forming means comprising two windows, one opposite the other, between which a film of fluid is formed. The film of fluid is irradiated through one of the windows and the transmitted radiation which passes through the other window is directed to a spectrophotometer for analysis.

This document is specifically concerned with the problem of how to keep the windows a specified distance apart during measurement of the. transmission spectrum of the fluid film, in order to avoid measurement errors caused by changes in the separation of the windows due to heat expansion of their holders when high temperature fluids are being analysed. This is achieved by supplying at least one of the windows with raised projections which are pressed against the other window during measurement to ensure a fixed separation between the windows equal to the height of the raised projections. The apparatus described in this document is therefore suitable only for performing transmission spectrum analysis of a fluid whose properties are invariable, and would not be suitable for use in a paint manufacturing process, where batches of paints having different physical properties need to be analysed.

Finally, U.S. Pat. No. 3,740,156 describes a photometric analyser sampling cell, for performing transmission spectrum analysis of molten or liquid plastics materials, the cell comprising a film forming means for forming a fluid film having a prespecified thickness in a sampling region, by trapping a sample of fluid between two coaxial windows, one of which is fixed and the other of which is moveable. The film is irradiated through one of the windows and the transmitted radiation passes through the other window and is directed to a photometric analyser. The apparatus described in this document is almost identical to that described in EP 0 302 009, the windows being held a fixed distance apart during measurement of the transmission spectrum of the fluid sample, the only difference being the manner in which this fixed distance is achieved.

OBJECT OF THE INVENTION

The object of the present invention is to provide a system and method for analysing characteristic properties of paints, enamels, dyes or other fluids, whether suspensions or emulsions, which overcome the above mentioned problems in the state of the art, and both significantly reduce the time required to measure said properties and increase the sensitivity of the measurement.

SUMMARY OF THE INVENTION

According to a first aspect of the present invention, a fluid analysis system, for analysing a specified physical characteristic of a fluid, comprises:

a film forming arrangement which may comprise any means for formng a fluid film;

a film irradiating arrangement which may comprise any means that is adapted to irradiate the film with electromagnetic radiation to produce an interaction radiation containing information associated with the specified physical characteristic of the fluid;

a receptor arrangement which may comprise any means, for receiving the interaction radiation; and a detector arrangement, which may comprise any means for detecting the interaction radiation, associated with the receptor arrangement.

The interaction radiation referred to above is that radiation produced by interaction of the radiation used to irradiate the fluid with the fluid itself.

The film forming arrangement comprises a sampling region defined between opposed fluid contact surfaces, the sampling region being in communication with a fluid inlet to permit feeding therein of the fluid, to form the fluid film having a thickness defined by the distance between the opposed fluid contact surfaces in the sampling region. The fluid contact surfaces are formed on respective contact portions which are mounted for controlled movement with respect to each other, to vary the relative positions of the contact surfaces. At least one of the contact surfaces is pervious to electromagnetic radiation, and the system further comprises a surface cleaning arrangement which may comprise any means for effecting cleaning of the pervious contact surface, as a result of the controlled movement of the contact portion.

For preference, the pervious contact surface is substantially planar, and the controlled movement of the contact portions with respect to each other includes a component parallel to the plane of the pervious contact surface.

For further preference, the controlled movement of the contact portions with respect to each other also includes a component perpendicular to the plane of the pervious contact surface, to vary the distance between the fluid contact surfaces. An actuator arrangement, which may comprise any means to effect the controlled movement of the contact portions with respect to each other, is operable on at least one of the contact portions and is responsive to a control signal from a system control means.

More preferably still, both the opposed fluid contact surfaces are pervious to electromagnetic radiation and the contact portions are movable between a first sampling position, in which the sampling region is defined between opposed fluid contact surfaces both of which are pervious to electromagnetic radiation, and a second sampling position, in which the sampling region is defined between opposed fluid contact surfaces, only one of which is pervious to electromagnetic radiation.

Preferably, the cleaning arrangement is mounted in the contact portion, or portions, opposite that/those on which the pervious contact surface, or surfaces, is/are formed and comprises a solvent resistant elastomeric blade.

For further preference, the sampling region is in communication with a fluid outlet, to permit flow of the fluid through the sampling region, and the fluid analysis system further comprises fluid flow control means, for controlling the flow rate of the fluid through the sampling region. Fluid flow control means may comprise a pump.

More preferably still, the film irradiating means comprises an electromagnetic radiation source in communication with an electromagnetic radiation directing means, for directing electromagnetic radiation from the source to the fluid film. The radiation directing means may be a fibre optic cable, as may the receptor means, and the radiation source may be a laser or an incandescent lamp.

For still further preference, the fluid analysis system according to the present invention comprises temperature and pressure control means, for controlling the temperature and the pressure of the fluid, and fluid temperature and pressure measurement means, for measuring the temperature and pressure of the fluid in the film forming means.

According to a second aspect of the present invention, a method for analysing a specified physical characteristic of a fluid, comprises the following steps:

(i) feeding a fluid into a sampling region defined between opposed fluid contact surfaces formed on respective contact portions, at least one of the fluid contact surfaces being pervious to electromagnetic radiation, and the distance between the fluid contact surfaces defining the thickness of the fluid film;

(ii) irradiating the fluid film with electromagnetic radiation to produce an interaction radiation containing information associated with the specified physical characteristic;

(iii) receiving the interaction radiation; and (iv) detecting the received interaction radiation the method comprising the step, before step (i), of actuating a surface cleaning arrangement, which may comprise any means for effecting cleaning of the pervious contact surface, to clean the pervious contact surface by moving the contact portions with respect to each other.

Preferably, the method according to the present invention further comprises, before executing step (i), the step of moving the contact portions with respect to each other to change the distance between the opposed fluid contact surfaces, to specify the thickness.

More preferably still, the method according to the present invention comprises the further steps of:

(a) measuring the pressure of the fluid in the sampling region and applying a force to the contact portions, in accordance with thee measured pressure, to oppose the force exherted on the opposed fluid contact surfaces by the fluid; and (b) measuring the temperature of the fluid in the sampling region, and adjusting the temperature of the fluid to a specified value if the measured temperature does not correspond thereto.

BRIEF DESCRIPTION OF THE DRAWINGS

The present invention will now be described in greater detail, by way of example, with reference to the accompanying drawings, in which.

DETAILED DESCRIPTION OF THE INVENTION

Figure 1:
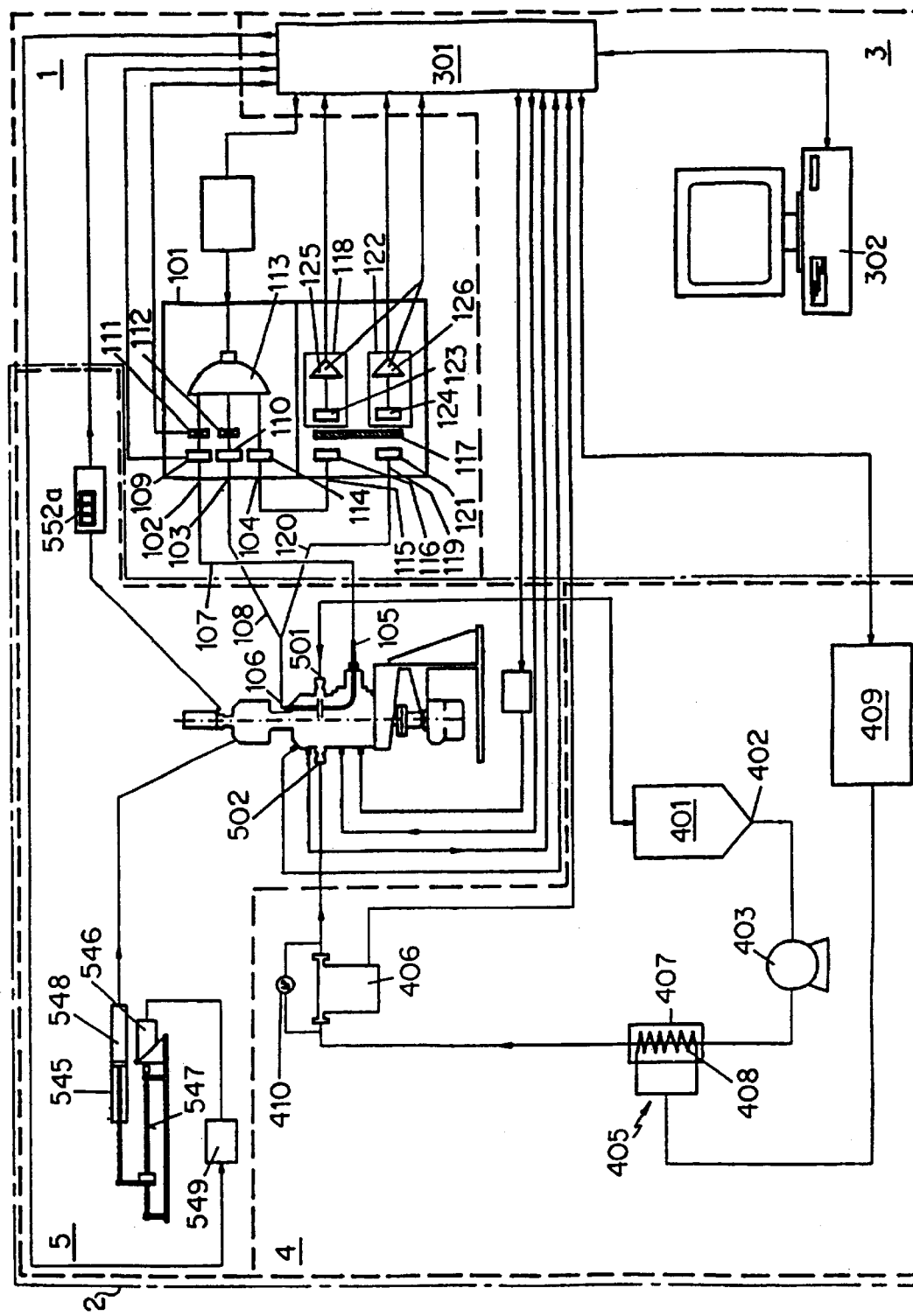
FIG. 1 shows a schematic diagram of a system for measuring characteristic properties of fluids, according to the present invention.

Referring first to FIG. 1 of the drawings, a fluid analysis system, according to the presently preferred embodiment of this invention, comprises an optical unit 1, for providing a source of electromagnetic radiation to a fluid analysis unit 2 and for sensing electromagnetic radiation emitted therefrom. Both optical unit 1 and fluid analysis unit 2 are connected to a system control unit 3, for data acquisition and control of the functions of units 1 and 2.

Optical unit 1 comprises a standard spectrometer 101 having three outputs 102, 103 and 104 for emitting electromagnetic radiation in the visible region of the electromagnetic spectrum. Outputs 102 and 103 are connected to inputs 105 and 106 of fibre optic cables 107 and 108 respectively. Electromagnetic radiation is provided to outputs 102, 103 and 104, via respective filter sets 109 and 110 and shutters 111 and 112, from a light source 113. Source 113 comprises an incandescent halogen lamp emitting a range of wavelengths from 400 to 700 nm, the supply for the lamp being electronically stabilised, and the lamp itself being monitored with respect to its performance so that it may be changed as soon as it goes below specification.

Filter sets 109, 110 and shutters 111, 112 are used to vary the colour (wavelength range) and intensity of the light emitted from outputs 102 and 103, so that various different measurements can be made of different properties of a number of different fluids.

Output 104 also receives light from source 113, via a filter set 114 and this light is directed by mirrors (not shown) to an input 115 and then through a fibre optic connector 116 and a monochromator disc 117 to a detector 118. This output serves as a reference for the measurement of the spectra received from fluid analysis unit 2.

Optical module 1 is also provided with an input 119 connected to a fibre optic cable 120 which directs light from fluid analysis unit 2 via a fibre optic connector 121 and monochromator disc 117 to a detector 122.

Filter sets 109, 110 and 114 comprise a series of coloured and neutral density filters which are used respectively to define the wavelength range under investigation and the intensity of the light reaching detectors 118 and 122. The intensity of the light received by detectors 118 and 122 is controlled using neutral density filters in order to enable the detectors to operate in their optimum condition, without saturation by high intensity light, or lack of resolution with low intensity light. The colour spectrum, reaching fluid analysis unit 2 from source 113, is chosen by using coloured filters in filter sets 109 and 110 to define a wavelength range of the light, so that a particular region of the spectrum may be chosen for detailed inspection.

Monochromator disc 117 consists of an interference filter that is rotated continually by a stepper motor (not shown) to allow transmission of a series of discrete wavelengths therethrough, depending on the rotational position of the disc. This has the effect of allowing detectors 118 and 122 to detect single frequency radiation and defines the wavelength resolution of spectrometer 101.

Detectors 118 and 122 comprise respective high sensitivity photo-diodes 123 and 124 connected to respective low noise amplifiers 125 and 126.

Fluid analysis unit 2, comprises a fluid control unit 4 which controls the physical properties of, and supplies a continuous flow of, the fluid under investigation, such as paint, to a fluid analysis cell 5.

Fluid control unit 4 comprises a storage tank 401 having an outlet 402 connected to a fluid circulation pump 403, and an inlet 404 connected to a fluid outlet 501 of fluid analysis cell 5. Fluid is pumped from storage tank 401 through a heat exchanger 405 to a coriolis type mass flow rate detector 406. Heat exchanger 405, used to control the temperature of the fluid so that it remains stabilised at a specified value during measurement in fluid analysis cell 5, comprises a coil (not shown) immersed in a bath of water 407, which has its temperature controlled using a heating element 408 supplied by a temperature control unit 409. Flow rate detector 406 is used to provide a measure of the mass flow rate of the fluid, and is also used, in conjunction with a differential pressure sensor 410, for the acquisition of data with respect to the density, direct temperature and viscosity of the fluid. Differential pressure sensor 410 measures the pressure difference across flow rate detector 406. The viscosity of the fluid is calculated using a standard equation which relates the instantaneous flow rate, density, temperature and the pressure difference across flow rate detector 406.

Flow rate detector 406 has an output connected to fluid analysis cell 5 at a fluid input 502.

Figure 2:
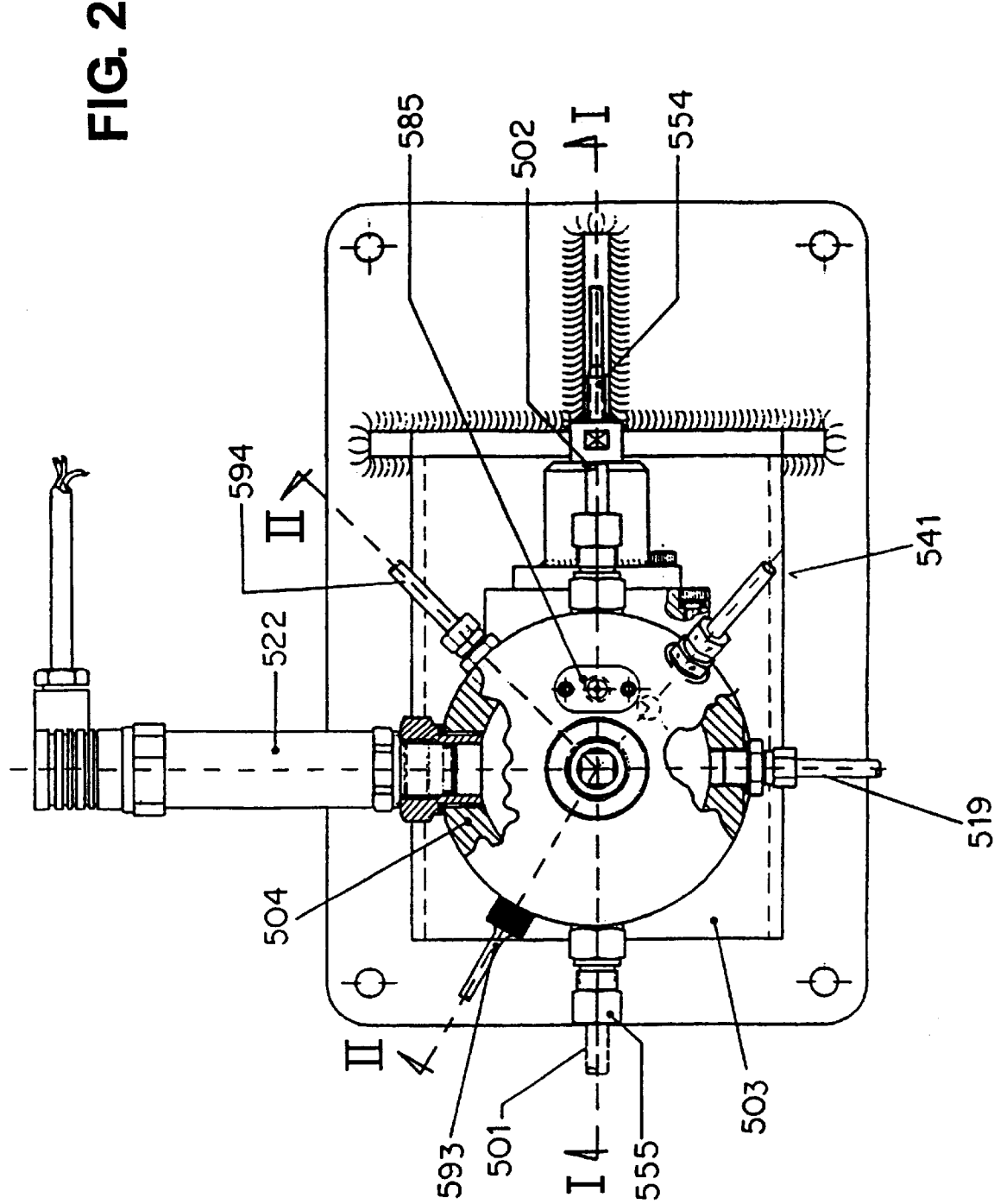
FIG. 2 shows a top plan view of a fluid analysis cell for use in the system for measuring characteristic properties of fluids, according to the present invention.
Figure 3:
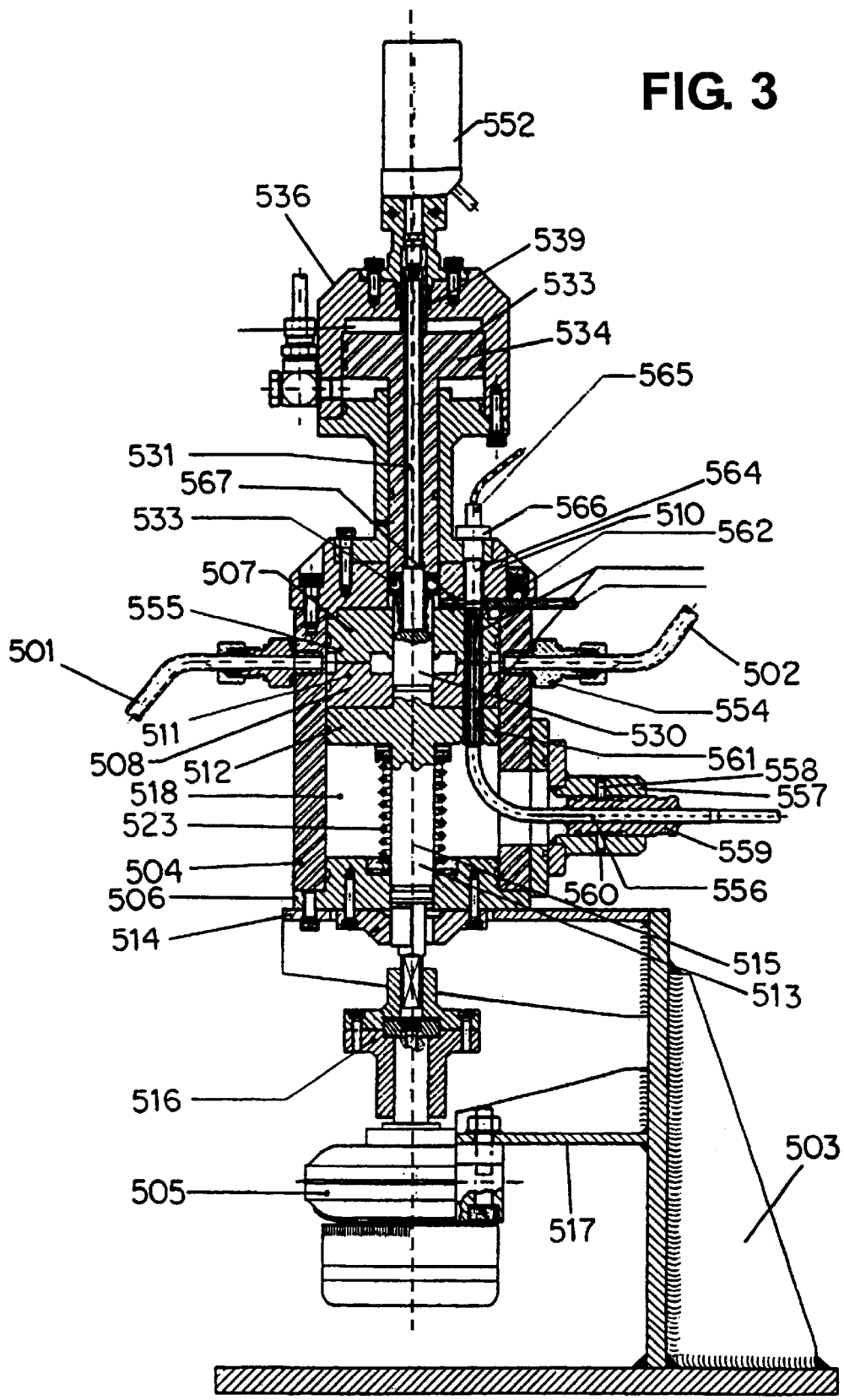
FIG. 3 shows a sectional view along line I—I of the fluid analysis cell shown in FIG. 2.
Figure 4:
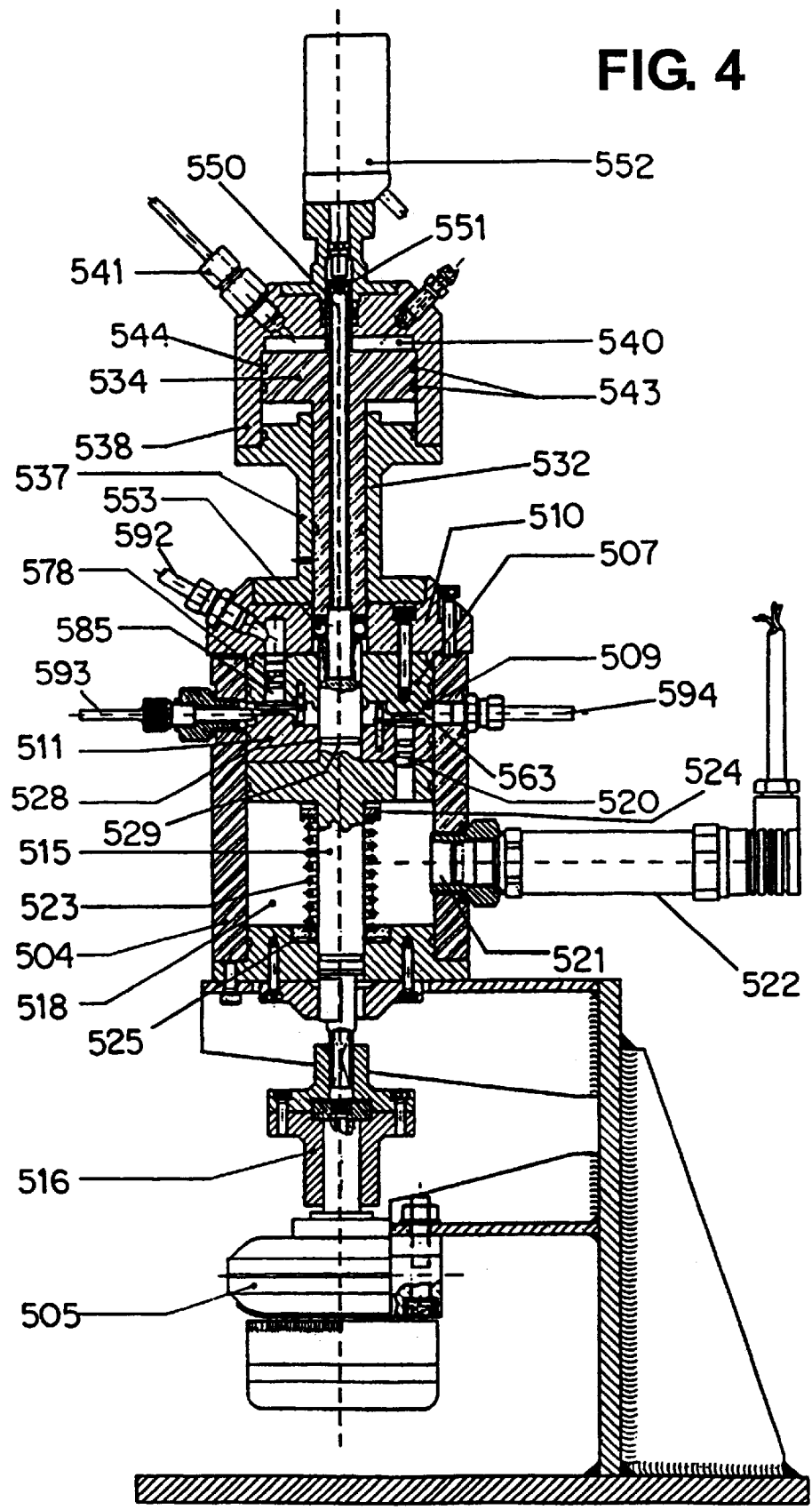
FIG. 4 shows a sectional view along line II—II of the fluid analysis cell shown in FIG. 2.

Referring now to FIGS. 2, 3 and 4, fluid analysis cell 5 comprises a base-plate 503, to which is mounted a fluid containment cylinder 504, and a rotatable pneumatic actuator 505. Cylinder 504 is mounted to base-plate 503 via a bottom-plate 506 and contains an upper disc 507 and a lower disc 508 between which is formed an analysis chamber 509. Upper disc 507 is fixedly mounted to cylinder 504 via a top-plate 510, and lower disc 508, which comprises an upper portion 511 and a lower portion 512, is free to move along the axis of cylinder 504 and to rotate therein. Lower portion 512 of lower disc 508 has a shaft 513 extending perpendicular to the plane of lower disc 508, from the centre thereof, both upwardly and downwardly. Upper portion 511 of lower disc 508, upper disc 507 and top-plate 510 are formed with a hole in their respective centres to allow the upwardly extending portion of shaft 513 to pass therethrough. The downwardly extending portion of shaft 513 extends through bottom-plate 506 and a horizontally extending portion 514 of base-plate 503, which are provided with respective holes in their centres to allow clearance of shaft 513 therethrough, and has a lower axle end 515 attached via a coupling 516 to actuator 505. Coupling 516 is attached to actuator 505, which is mounted on a further horizontally extending portion 517 of base-plate 503, to enable rotational movement of shaft 513 about its longitudinal axis while at the same time allowing shaft 513 to move vertically.

The inner wall of cylinder 504, lower surface of lower portion 512 of lower disc 508 and upper surface of bottom-plate 506 form a lower pressure chamber 518 which is supplied, during use of fluid analysis cell 5, with pressurised air through pressure inlet 519. Lower pressure chamber 518 serves both to actuate an upper disc cleaning mechanism 520 (the function of which will be described in detail later in the detailed description) and to enable a controlled upwards pressure to be exhorted on lower disc 508. Also provided in lower pressure chamber 518 is an outlet 521 to a pressure sensor 522 which measures the pressure in the chamber. The need for both pressure inlet 519 and sensor 522 will become clear later in the description.

A compression spring 523 is housed longitudinally within lower pressure chamber 518, around the downwardly extending portion of shaft 513, having its upper and lower ends; attached to respective compression plates 524 and 525 in the form of an annulus. Lower compression plate 525 is held within a depression in the upper surface of bottom-plate 506, and upper compression plate 524 abuts the lower surface of lower portion 512 of lower disc 508, exherting an upwards force on lower disc 508.

An o-ring 526 is located within an annular slot 527 in shaft 513, towards the lower end of the downwardly extending portion thereof, to form a pressure seal against leakage of compressed air from lower pressure chamber 518. Two o-rings 528 are also located in respective annular grooves 529 located along the upwardly extending portion of shaft 513 between the upper and lower surfaces of upper portion 511 of lower disc 508, and the upper and lower surfaces of upper disc 507. O-rings 528 prevent leakage of the fluid under analysis from analysis chamber 509.

Referring to FIGS. 3 and 4, upper portion of shaft 513 has its end 530 abutting an adjustment rod 531 which is housed within the shaft 532 of a piston 533. Piston 533 has wa head 534, integral with shaft 532, in the form of a horizontal disc from the centre of the lower surface of which shaft 532 extends. A guide shaft 535 is also provided, integral with and extending vertically upwards from the centre of the upper surface of piston head 534.

Piston 533 is movably contained within a piston housing 536, attached to top-plate 510 of fluid analysis cell 5. Piston housing 536 comprises a piston shaft housing 537, attached to a cylindrical piston head housing 538 which is open at its lower end and closed at its upper end. The closed upper end of piston head housing 538 is formed with a vertical bore 539 on the cylinder axis, to allow guide shaft 535 to pass therethrough.

An upper pressure chamber 540 is formed between the upper surface of piston head 534 and the inner cylindrical surface and inner surface of the closed upper end of piston head housing 538. Upper pressure chamber is supplied, during use of fluid analysis unit 2, with a hydraulic fluid such as oil, through a fluid inlet 541 (shown in FIG. 4). The hydraulic fluid exherts pressure on piston 533 to move it downwards, together with adjustment rod 531, and thereby move lower disc 508 of fluid analysis chamber 509 away from upper disc 507.

A drain 542 is also provided in piston head housing 538, to allow hydraulic fluid to be drained from upper pressure chamber 540 so that the hydraulic fluid in the system can be changed.

In order to seal upper pressure chamber 540 against leakage of hydraulic fluid therefrom, a series of o-rings 543 are provided on piston 533. Each o-ring 543 is held within a respective annular slot 544 on piston 533, two on piston head 534, one on piston shaft 532 and two on guide shaft 535.

Hydraulic fluid is supplied to pressure chamber 540 from a hydraulic piston 545, shown in FIG. 1, which is actuated by a stepper motor 546. Stepper motor 546 is used to turn a screw threaded rod 547 which, when rotated in one direction, translates piston 545 within a fluid reservoir 548 to supply hydraulic fluid to upper pressure chamber 540, and when rotated in the opposite direction translates piston 545 to drain the hydraulic fluid from pressure chamber 540.. Stepper motor 546 is connected to system control unit 3 via a stepper motor control 549, for control of the pressure applied to analysis cell piston 533.

Referring again to FIGS. 3 and 4, adjustment rod 531 has its upper end 550 abutting a feeler gauge 551 of a micrometer 552. Rotary coupling 551 allows adjustment rod 531 to rotate with lower disc 508 of fluid analysis chamber 509 without rotating micrometer 552. Vertical movement of adjustment rod 531, due to movement of piston 533, is sensed by gauge 552 which provides an accurate reading, to within 0.1 of a micron, of the distance moved by adjustment rod 531 from a zero position. As will be seen later in the description, said zero position corresponds to the position in which upper and lower discs, 507 and 508, of analysis chamber 509 are abutting. Micrometer 552 is connected, via an optical path indicator 552a which provides the operator with a reading of the optical path, to system control unit 3.

Movement of piston 533 is transmitted directly to lower disc 508 of fluid analysis chamber 509, due to the provision of an axial bearing 553 in top-plate 510. Axial bearing 553 allows vertical movement of shaft 513 to be transmitted to adjustment rod 531, while at the same time enabling free rotational movement of the shaft.

Fluid analysis chamber 509 will now be described in greater detail with reference to FIGS. 5 and 6 in conjunction with FIGS. 3 and 4. Referring first to FIG. 3, fluid containment cylinder 504 is provided with a fluid inlet 554 and a fluid outlet 555 diametrically opposed thereto. Fluid inlet 554 and outlet 555 allow the fluid to be analysed to be fed into analysis chamber 509. Fluid analysis is made by illuminating the fluid in analysis chamber 509 with electromagnetic radiation. In the presently preferred embodiment of this invention optical radiation is used, provided by light source 113 in optical unit 1 of the system.

As mentioned previously, light from source 113 is transmitted to fluid analysis unit 2 through fibre optic cables 107 and 108, for transmission and reflection analysis respectively. Fibre optic cable 107 is used to direct light upwardly through fluid analysis chamber 509 and is directed into fluid analysis cell 5 through a flexible fibre guide 556 which enters lower pressure chamber 518 through a pressure coupling 557 in the wall of containment cylinder 504. Fibre guide 556 enters radially into lower pressure chamber 518 and curves upwards to abut the lower surface of lower portion 512 of lower disc 508. Pressure coupling 557 comprises a coupling plug 558 held within a mount 559 attached to the outer cylindrical surface of fluid containment cylinder 504. Coupling plug 558 is sealed around fibre guide 556 and is provided on its external cylindrical surface with a series of annular slots 558 having respective o-rings (not shown). Plug 558 is held within mount 559 by adjustment screws 560 which can be loosened to allow adjustment of the position of fibre guide 556.

Figure 5:
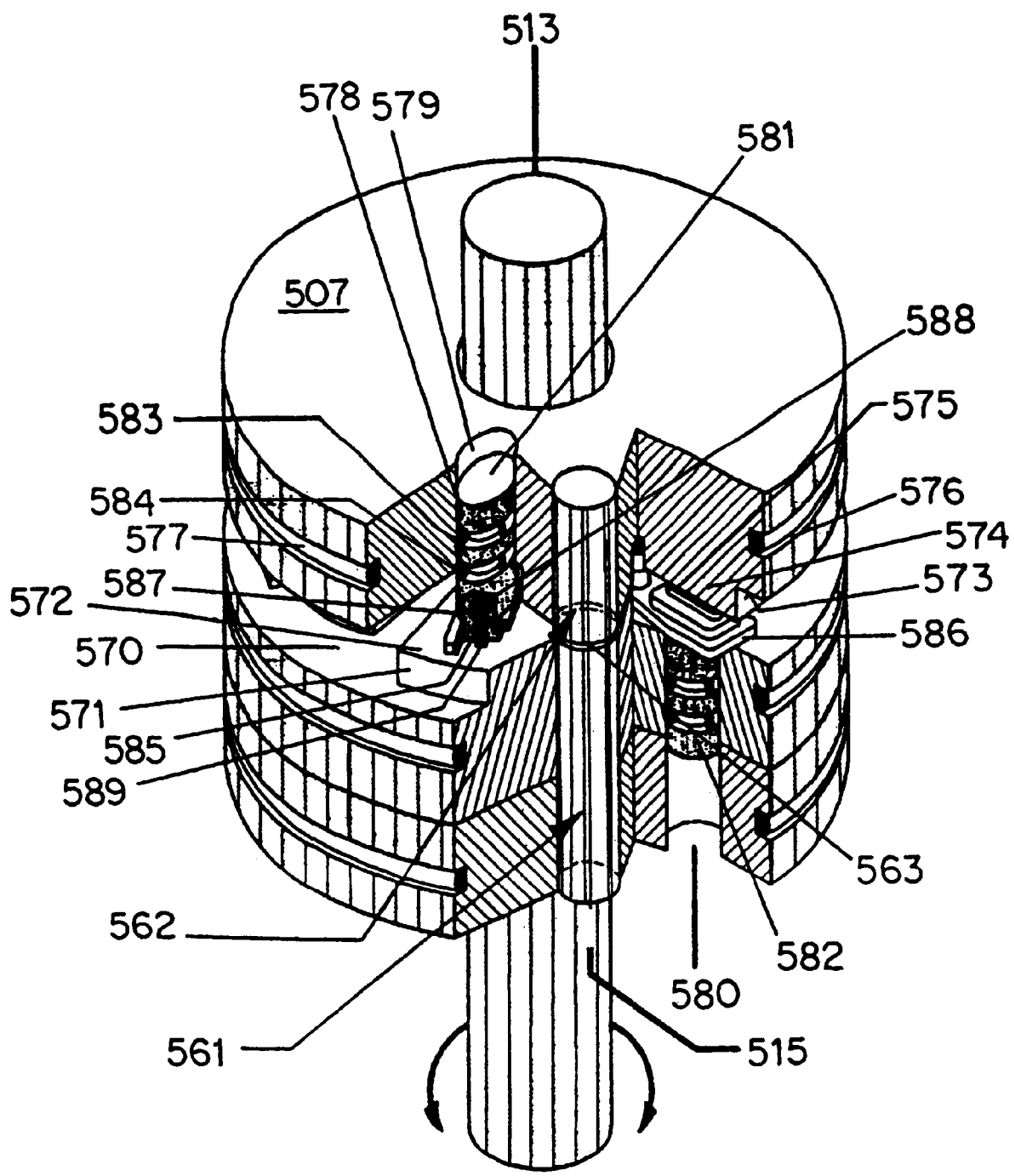
FIG. 5 shows a perspective cutaway view of a fluid analysis chamber for use in the fluid analysis cell shown in FIGS. 2, 3 and 4.

Lower disc 508 of analysis chamber 509 is provided with an optical window 561, extending vertically therethrough, as shown in FIG. 3 and in greater detail in FIG. 5. Window 561, which has a cylindrical form, has planar parallel upper and lower ends which are flush with the upper and lower surfaces respectively of lower disc 508.

As shown in FIGS. 3 and 5, upper disc 507 of fluid analysis chamber 509 is also provided with an optical window 562, extending vertically therethrough and having planar parallel lower and upper ends flush with respective lower and upper surfaces of upper disc 507. In the configuration shown in FIGS. 3 and 5 optical windows 561 and 562 are aligned with each other. This configuration is used for transmission measurements where light is transmitted through a fluid analysis region 563, defined between planar lower surface of window 562 in upper disc 507 and the upper surface of upper portion 511 of lower disc 508, which, in the case of transmission, corresponds to the upper surface of optical window 561.

Referring to FIG. 3, the cylinder axis of optical window 562 is aligned with a bore 564 in top-plate 510 into which is fitted a fibre optic cable holder 565. Cable holder 565 comprises a hollow cylinder having an outer diameter slightly less than the diameter of bore 564, so as to provide a tight fit of holder 565 within bore 564. Fibre optic cable 108 is held within cable holder 565 with its end parallel with the lower end thereof, and cable holder 565 is held away from window 562 by a stop 566 attached near the upper end thereof.

A cavity 567 is formed between top-plate 510 and upper surfaces of disc 507 and the wall of containment cylinder 504, in the region of window 562 and bore 564. Cavity 567 is in the form of a horizontal slot, extending from the outer cylindrical surface of containment cylinder 504 to the wall of the bore containing shaft 513, but not into said bore. A calibration plate 568 is movably contained within cavity 567 by a roller bearing 569, and is free to move in the horizontal plane between a position in which it lies between optical window 562 and bore 564, and in which it does not. The upper surface of calibration plate 568 is provided with a coating, corresponding to a standard desired reflection spectrum, and is used to calibrate the system during analysis of the reflection characteristics of the fluid under analysis.

Figure 6:
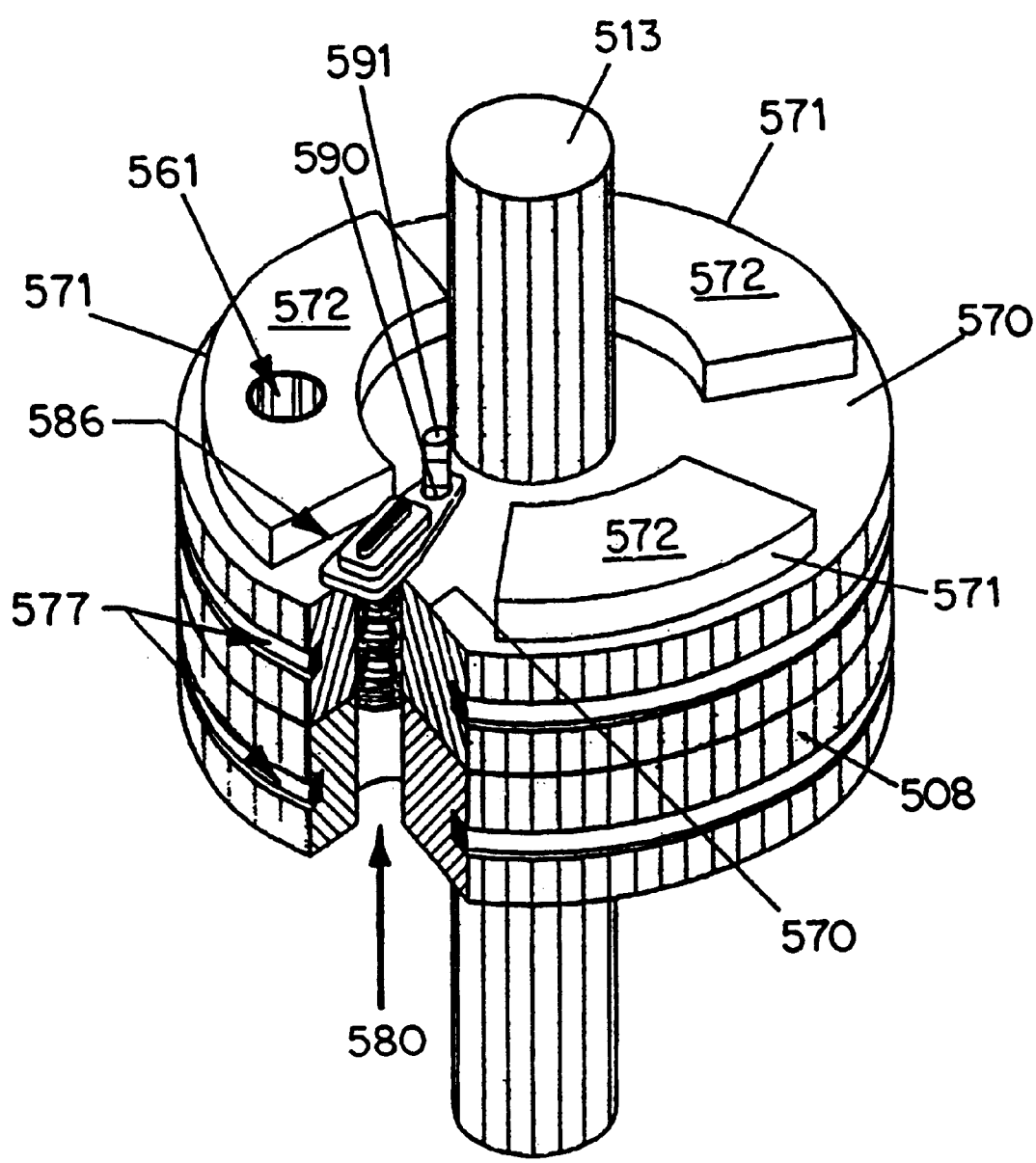
FIG. 6 shows a perspective cutaway view of the lower disc of the fluid analysis chamber shown in FIG. 5, rotated through an angle of 60° in a clockwise direction.

Referring now to FIG. 6, the upper end of upper portion 511 of lower disc 508 of fluid analysis chamber 509 is formed with a planar end surface region 570 which has three equi-spaced annular segments 571 protruding therefrom. Each annular segment 571 has side faces extending perpendicularly from planar end surface region 570 a short distance to form respective planar segment surfaces 572 which are parallel to surface region 570. Note that optical window 561 is positioned in the radial centre of one of segments 571 with its upper planar surface lying in the plane of segment surfaces 572. Optical window 561 is off-set to the left of the bisector of the segment when viewed from the radial centre of lower disc 508.

Figure 7A:
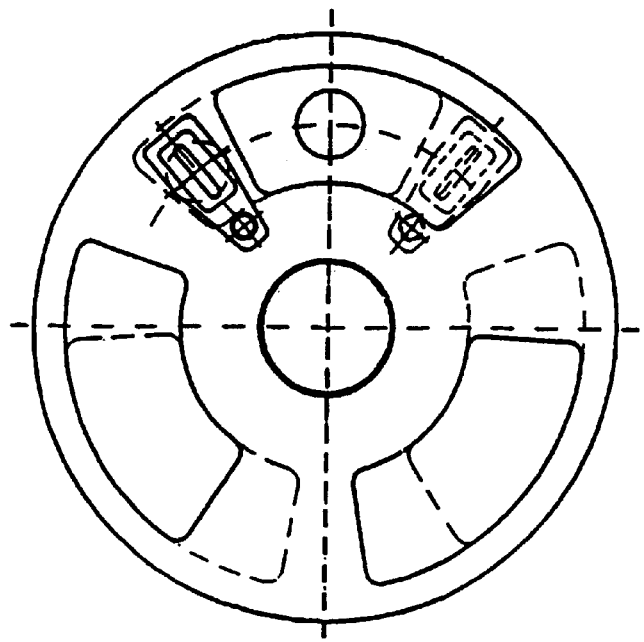
FIG. 7a shows a top plan sectional view of the fluid analysis chamber shown in FIG. 5.
Figure 7B:
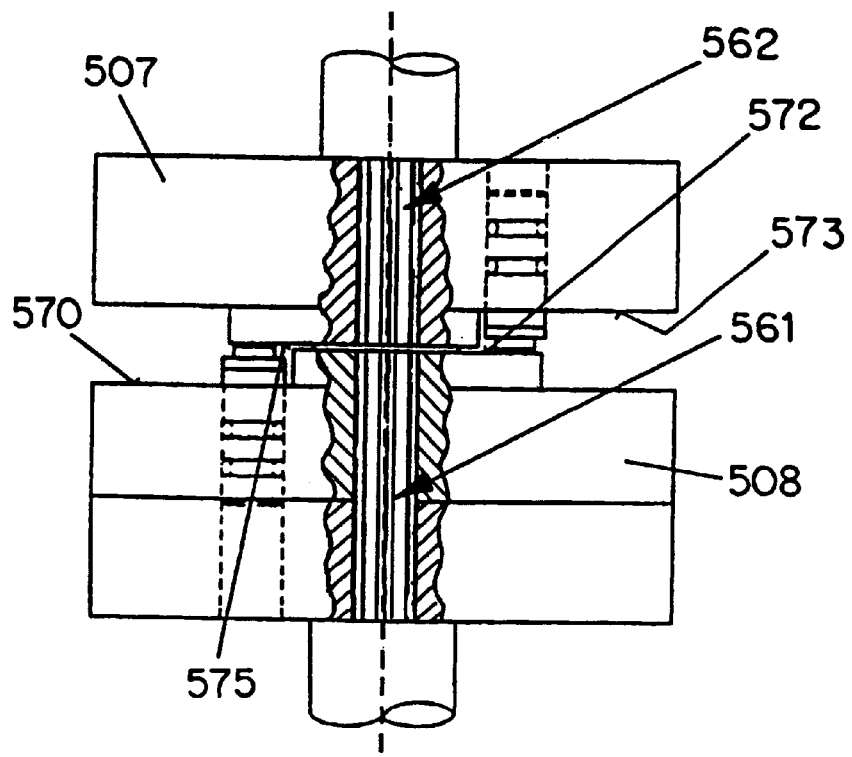
FIG. 7b shows a side plan sectional view of the fluid analysis chamber shown in FIG. 5.
Figure 8A:
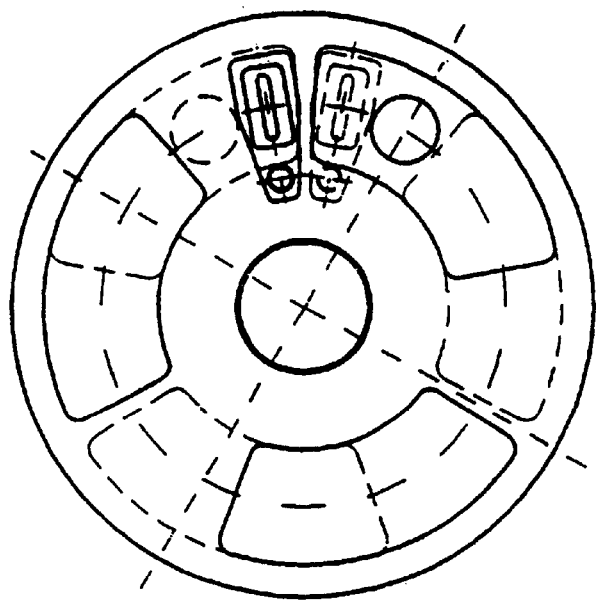
FIG. 8a shows a top plan sectional view of the fluid analysis chamber shown in FIG. 5 with the lower disc rotated as shown in FIG. 6.
Figure 8B:
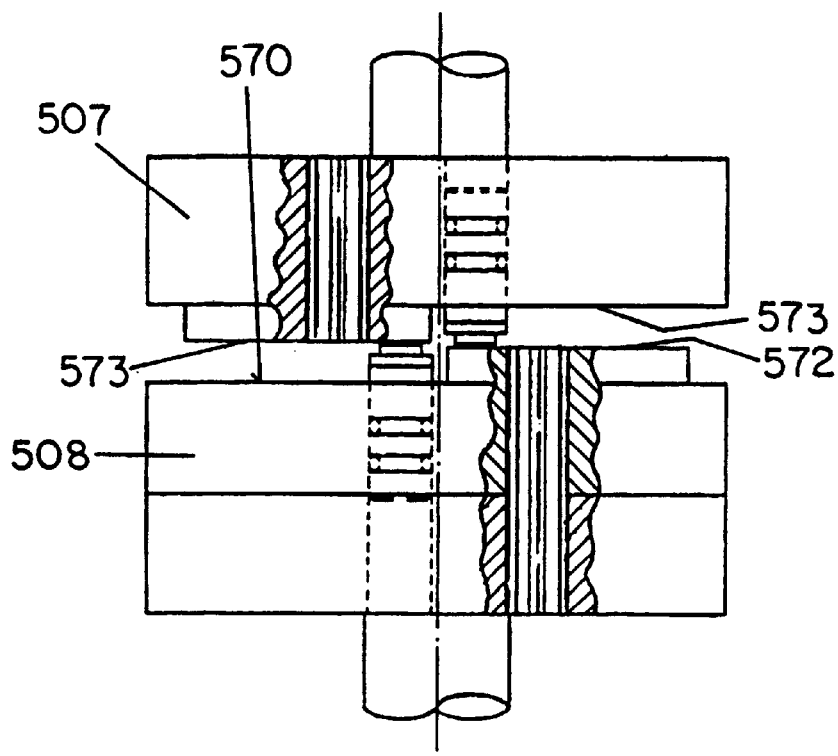
FIG. 8b shows a side plan sectional view of the fluid analysis chamber shown in FIG. 5 with the lower disc rotated as shown in FIG. 6.

As can be seen in FIGS. 5, 7 and 8, the lower end of upper disc 507 is also formed with a planar end surface region 573 having three equi-spaced annular seo-gments 574 protruding therefrom. Each of annular segments 574 has side faces extending perpendicularly from planar surface region 573 to form respective planar segment surfaces 575 parallel to planar surface region 573. Note that, as with lower disc 508, optical window 562 is positioned in the radial centre of one of segments 574 with its lower planar surface lying in the plane of segment surfaces 575. However, in the case of upper disc 507, optical window 562 is off-set to the right of the bisector of the segment when viewed from the radial centre of disc 507.

Annular segments 571 and 574, containing respective optical windows 561 and 562, are positioned opposite one another when fluid analysis chamber 509 is configured for transmission analysis, so that the axes of optical windows 561 and 562 correspond, as shown in FIG. 7.

In the case when fluid analysis chamber 509 is configured for reflection analysis, lower disc 508 is rotated through an angle of 60°, with respect to its position in the transmission analysis configuration, so that the axis of optical window 562 in upper disc 507 is aligned with a part of planar surface region 570, as shown in FIG. 8.

Upper and lower discs 507 and 508 are formed with grooves 576 around their outer circumference, one on upper disc 507 and one on each portion 511 and 512 of lower disc 508, for holding o-rings 577 which form a seal between discs 507 and 508 and the inner wall of fluid containment cylinder 504.

With reference to FIG. 4, upper and lower disc cleaning mechanisms 520 and 578 are provided in lower and upper discs 508 and 507 respectively, for cleaning the segment surfaces 575 and 572 containing optical windows 562 and 561. Cleaning mechanisms 520 and 578, which are shown in greater detail in FIGS. 5 and 6, comprise oval shaped bores 579 and 580 in upper and lower discs 507 and 508 respectively, each containing a respective oval shaped rod 581 and 582, which is moveable therein. Bores 579 and 580 are positioned such that they extend vertically through discs 507 and 508, entering analysis chamber 509 in those parts of respective planar end surface regions 573 and 570 to the right of and to the left of corresponding annular segments 574 and 571 respectively. Rods 581 and 582 are provided with grooves 583 around their circumferences, spaced about the longitudinal centre of the rods, each of grooves 583 holding an o-ring 584 to provide a pressure seal against leakage of fluid from analysis chamber 509, or leakage of the pressurised air used to actuate the cleaning mechanisms.

Each of rods 581 and 582 has a respective head portion, 585 and 586, each formed with a tongue 587, which is fixed in a, groove 588 in the ends of rods 581 and 582. A vertical slot 588, parallel with tongue 587, is provided in head portions 585 and 585 into each of which is fixed an elastomeric blade 589 which is resistant to solvents. Each of head portions 585 and 586 has a plate-like extension, extending inwardly to the radial centres of discs 507 and 508, and provided with a vertical. hole 590. Vertical holes 590 are adapted to fit movably on corresponding guide rods 591, which extend perpendicularly from planar surface end regions 570 and 573, to hold head portions 585 and 586 aligned with their longitudinal axes along a radius of discs 507 and 508.

As mentioned previously, upper disc cleaning mechanism 520 is actuated by compressed air in lower pressure chamber 518 which forces rod 582 upwards, to press blade 589 against the upper disc segment surface 575 containing the lower end surface of optical window 562. In a similar manner, as shown in FIG. 4, lower disc cleaning mechanism 578 is actuated by compressed air, which is supplied continually through a pressure inlet 592 provided in top-plate 510 of fluid containment cylinder 504, to force rod 581 downwards, pressing blade 589 against the lower disc segment surface 572 containing the upper end surface of optical window 561.

With reference to FIG. 4, a fluid temperature sensor 593 and a fluid pressure sensor 594 are also provided in fluid analysis chamber 509, so that the temperature and pressure of the fluid under analysis in fluid analysis region 563 can be monitored to ensure stability of the measurement conditions.

The entire system is controlled by system control unit 3, which comprises a programmable microprocessor 301 connected to a microcomputer 302, for operator control thereof. System control unit 3 receives input signals from optical unit 1, from shutters 111 and 112, filter sets 109 and 110, and respective amplifiers 125 and 126 of photo-diodes 124 and 125, and provides a control signal for source 113. Control unit 3 is also programmed to control filter sets 109, 110, 114 and 115, as well as shutters 111 and 112, and monochromater disc 117, so that optical unit 1 can automatically scan through the required wavelength range.

Control unit 3 also controls the functions of fluid analysis unit 2, by sending control signals to fluid control unit 4 and to fluid analysis cell 5, depending on the required system parameters and feedback signals received from the various components of fluid control unit 4 and analysis cell 5. The connections between the various components of fluid control unit 4 and fluid analysis cell 5, and system control unit are shown in FIG. 1.

With reference to FIGS. 1 to 8, the cycle of analysing a particular fluid comprises the following steps.

Initially, the settings for the physical parameters, such as the temperatures and pressures, of the fluid to be analysed are determined. System control unit 3 then initiates a self-check of its operating system and checks optical unit 1 and fluid analysis unit 2 to ensure that all components are in working order and are set correctly.

Once the parameter, system and component checks have been completed, system control unit 3 sends a signal to hydraulic piston stepper motor control 549 to actuate stepper motor 546 which turns screw threaded rod 547 so that piston 545 withdraws any hydraulic fluid from upper pressure chamber 540 of fluid analysis cell 5. Meanwhile, compressed air is supplied to lower pressure chamber 518, acting in conjunction with compression spring 523 to force lower disc 508 upwards against upper disc 507. When this happens, the optical path through fluid analysis region 563 is zero. With lower disc 508 pressed against upper disc 507 micrometer 552 is set at zero, thus setting a zero point reference for all other measurements.

In order to begin analysis of the fluid stored in storage tank 401, system control unit sends a signal to stepper motor control 549 to actuate stepper motor 546 so that rod 547 is rotated through a specified number of turns, depending on the required optical path distance between upper and lower discs 507 and 508. Note that the required optical path distance is determined by the opacity of the fluid under analysis, for a highly opaque fluid, in order to have sufficient bandwidth for transmission measurements, the fluid film must be thin, the optical path distance being correspondingly small. Rotation of rod 547 moves hydraulic piston 545 to force hydraulic fluid from fluid reservoir 548 into upper pressure chamber 540. This produces a pressure in upper pressure chamber 540 which forces piston 533 downwards, thereby moving lower disc 508 away from upper disc 507, until the pressure in upper pressure chamber 540 balances that in lower pressure chamber 518, due to the combined pressures exherted by the compressed air and compression spring 523. The distance moved by lower disc 508 is continuously measured by micrometer 552, via adjustment rod 531 and feeler gauge 551, and the optical path reading is displayed on optical path indicator 552a.

With the optical path set at the desired value, the fluid under analysis is pumped, by circulation pump 403, from storage tank 401 through heat exchanger 405, where it is heated to the required temperature for analysis. The required temperature is calculated after measurement of the viscosity of the fluid by flow rate detector 406 and differential pressure sensor 410, and the flow rate and temperature of the fluid are varied accordingly, until the required values are obtained.

As the fluid flows through fluid analysis chamber 509 of fluid analysis cell 5, temperature sensor 593 and pressure sensor 594 monitor the temperature and pressure of the fluid passing through fluid analysis region 563. The monitored values of temperature and pressure are compared, in system control unit 3, with the desired values and adjustments are automatically made, to circulation pump 403 and heating element 408 of heat exchanger 405, so that the required values are attained.

Due to the pressure differential across fluid inlet 502, as the fluid enters analysis chamber 509, the fluid flowing through analysis chamber 509 is slightly pressurised and therefore exherts a downward force on lower disc 508. To avoid, this effect, a pressure differential of 2 $N/cm^2$ is maintained between fluid analysis chamber 509 and lower pressure chamber 518. Pressure sensors 594 and 522 in fluid analysis chamber 409 and lower pressure chamber 518 measure the pressure difference and, any variation from the set pressure differential is compensated by system control unit 3, which sends a signal to regulate pressure inlet valve 519. In this way, there is continuous feedback, which ensures that the optical path remains fixed at the required value.

The optical path between upper and lower discs 507 and 508 is monitored continuously by micrometer 552 and, if necessary, is readjusted by varying the amount of hydraulic fluid in upper pressure chamber 540.

Once all the physical parameters of the fluid and the system have been established, analysis of the fluid can begin. In the specific embodiment described here, measurements of the absorption spectrum of the fluid are made, both in transmission and reflection.

In order to make the transmission measurements, upper and lower discs 507 and 508 are positioned so that optical windows 561 and 562 are aligned vertically across fluid analysis region 563. Alignment is made by actuation of rotatable pneumatic actuator 505, which is set to rotate shaft 513 of lower disc 508 between a first position, in which optical windows 561 and 562 are aligned, and a second position, having an angle of 60° with respect to the first position. Actuation of actuator 505 is made automatically by system control unit 3, depending on the type of measurement to be made.

With optical windows 561 and 562 aligned, system control unit 3 activates optical unit 1 to direct light from source 113 via fibre optic cable 107 into fluid analysis cell 5, through pressure coupling 557 holding fibre guide 556. Fibre guide 556 directs the light from source 113, through optical window 561 in lower disc 508, into fluid analysis region 563 where it interacts with the fluid film formed between optical windows 561 and 562. The light interacts with the fluid, certain wavelengths of the light being absorbed by components of the fluid, and the light that remains passes through optical window 562 in upper disc 507. This transmitted light is collected by fibre optic cable 120 and is directed into optical unit 1 through input 119, where it undergoes spectrum analysis to produce a signal representing the absorption spectrum, in transmission, of the fluid. In the preferred embodiment of the present invention, system control unit 3 has a reference absorption spectrum recorded therein, and compares the measured absorption spectrum with this reference. If there is a difference between the spectra, system control unit 3 iteratively adjusts the various components in the fluid under analysis, continually updating the absorption measurement, to obtain the desired characteristic properties of the fluid.

Once the transmission measurements have been made, system control unit 3 activates pneumatic actuator 505, which rotates shaft 513 of lower disc 508 through 60°. As lower disc 508 rotates about its axis, cleaning mechanisms 520 and 578, which are continually activated, scrape respective elastomeric blades 589 across optical windows 561 and 562, effecting cleaning thereof. With lower disc 508 rotated through 60° with respect to the transmission measurement position, reflection measurements of the fluid can be made. In this case, system control unit 3 activates source 113 in optical unit 1, and opens shutter 112. This allows light from source 113 to be directed, via fibre optic cable 108, held in cable holder 565 in fluid analysis cell 5, through optical window 562 in upper disc 507, into fluid analysis region 563.

Fluid analysis region 563 is, in this instance, defined between segment surface 575, of upper disc 507, and planar end surface region 570, of lower disc 508. These surfaces are spaced at least 6 mm from each other, providing sufficient fluid film thickness for complete absorption of the light coming from optical window 562, there being no reflection of light from surface region 570. The light entering fluid analysis region 563 is absorbed by the fluid and re-radiated in all directions after interaction. A part of this re-radiated light returns through window 562 and is collected by fibre optic cable 108. Fibre optic cable 108 is, as mentioned previously, formed with two sets of optical fibres, one for directing light from optical unit 1 to fluid analysis region 563, and the other for collecting light reflected by the fluid flowing through fluid analysis chamber 509. This reflected light is collected by fibre optic cable 108 and is directed into optical unit 1 through input 106, where it undergoes spectrum analysis to produce a signal representing the absorption spectrum, in reflection, of the fluid.

In order to obtain a reference value for the reflection measurements, calibration plate 568 is moved into cavity 567 where its upper surface is illuminated by light from fibre optic cable 108. Light reflected from the coated surface of calibration plate 568 is collected by cable 108 and directed into optical unit 1, where it undergoes spectral analysis, and forms the basis for the analysis of the reflection spectrum obtained from the fluid.

Analysis of transmission and reflection measurements is carried out by microprocessor 301 and displays the results of the analysis on micro-computer 302.

It should readily be appreciated that the invention, as described above, can be carried out in a number of different embodiments. Simple variations in the apparatus of the invention and the method for carrying out the invention will be self evident to those versed in the art. The apparatus of the invention can be adapted to carry out a variety of different measurements of the characteristic properties of fluids, one of which being particle sizing which has important applications in many industries. In order to carry out particle sizing measurements of fluid films, the apparatus of the present invention may be modified simply, by orienting optical windows 561 and 562, so that scattered light from particles within the fluid can be detected. In this case fluid analysis cell 5 can be used in conjunction with either light or laser sources, to provide a measurement of the particle size distribution in the fluid. Such an analysis is extremely useful in the paint industry where a large number of paints comprise particles in suspension. Apart from changes to the orientation of optical windows 561 and 562, and to the radiation source used to irradiate the fluid, advantageous physical changes to the device itself will be apparent to those skilled in the art, and as such, the scope of the present invention should be limited only by the terms and interpretation of the following claims.

What is claimed is:

1. A fluid analysis system, for analyzing a specified physical characteristic of fluid, comprising:
    a film forming means, for forming a fluid film;
    a film irradiating means, adapted to irradiate said film with electromagnetic radiation to produce an interaction radiation containing information associated with said specified physical characteristic of said fluid;
    a receptor means, for receiving said interaction radiation; and
    a detector means, associated with said receptor means, for detecting said interaction radiation,
    wherein said film forming means includes a sampling region defined between opposed fluid contact surfaces, said sampling region being in communication with a fluid inlet to permit feeding therein of said fluid, to form said fluid film having a thickness defined by the distance between said opposed fluid contact surfaces in said sampling region, said fluid contact surfaces being formed on respective contact portions which are mounted for controlled movement with respect to each other, to vary the relative positions of said contact surfaces, at least one of said contact surfaces being pervious to electromagnetic radiation, and said system further comprising of surface cleaning means which effects cleaning of said at least one pervious contact surface, as a result of said controlled movement.

2. A fluid analysis system according to claim 1, characterized in that said pervious contact surface is substantially planar, and said controlled movement of said contact portions with respect to each other includes a component parallel to the plane of said pervious contact surface.

3. A fluid analysis system according to claim 1, characterized in that said controlled movement of said contact portions with respect to each other includes a component perpendicular to the plane of said pervious contact surface, to vary the distance between said fluid contact surfaces.

4. A fluid analysis system according to claim 1, characterized by further comprising actuator means operable on at least one of said contact portions to effect said controlled movement.

5. A fluid analysis system according to claim 4, characterized in that said actuator means is responsive to a control signal from a system control means.

6. A fluid analysis system according to claim 1, characterized in that both said opposed fluid contact surfaces are pervious to electromagnetic radiation.

7. A fluid analysis system according to claim 6, characterized in that said contact portions are movable between a first sampling position, in which said sampling region is defined between opposed fluid contact surfaces both of which are pervious to electromagnetic radiation, and a second sampling position, in which said sampling region is defined between opposed fluid contact surfaces, only one which is pervious to electromagnetic radiation.

8. A fluid analysis system according to claim 1, characterized in that said cleaning means is mounted in the contact portion opposite that on which said at least one pervious contact surface is formed.

9. A fluid analysis system according to claim 1, characterized in that said cleaning means comprises an elastomeric blade that is resistant to solvents.

10. A fluid analysis system according to claim 1, characterized in that said sampling region is in communication with a fluid outlet, to permit flow of said fluid through said sampling region.

11. A fluid analysis system according to claim 10, characterized by further comprising fluid flow control means, for controlling the flow rate of said fluid through said sampling region.

12. A method for analyzing a specified physical characteristic of a fluid, comprising the steps of:
    (i) feeding a fluid into a sampling region defined between opposed fluid contact surfaces formed on respective contact portions, at least one of said fluid contact surfaces being pervious to electromagnetic radiation, and the distance between said fluid contact surfaces defining the thickness of said fluid film;
    (ii) irradiating said fluid film with electromagnetic radiation to produce an interaction radiation containing information associated with said specified physical characteristic;
    (iii) irradiating said interaction radiation; and
    (iv) detecting said received interaction radiation characterized by comprising the step, before said step (i), of actuating a surface cleaning means, to clean said at least one pervious contact surface by moving said contact portions with respect to each other.

13. Method according to claim 12, characterized by further comprising the step, before said step (i), of moving said contact portions with respect to each other to change the distance between said opposed contact surfaces, to specify said thickness.

* * * * *